United States Patent
Wen et al.

(10) Patent No.: US 11,304,907 B2
(45) Date of Patent: *Apr. 19, 2022

(54) PHARMACEUTICAL COMPOSITIONS CONTAINING A DGAT1 INHIBITOR

(71) Applicant: Novartis AG, Basel (CH)

(72) Inventors: Hong Wen, North Potomac, MD (US); Natrajan Kumaraperumal, Wayne, NJ (US); Richard Nause, Morristown, NJ (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/835,921

(22) Filed: Mar. 31, 2020

(65) Prior Publication Data

US 2020/0230062 A1 Jul. 23, 2020

Related U.S. Application Data

(63) Continuation of application No. 15/968,104, filed on May 1, 2018, now Pat. No. 10,646,446, which is a continuation of application No. 15/262,056, filed on Sep. 12, 2016, now abandoned, which is a continuation of application No. 14/805,919, filed on Jul. 22, 2015, now abandoned, which is a continuation of application No. 13/825,919, filed as application No. PCT/US2011/056275 on Oct. 14, 2011, now abandoned.

(60) Provisional application No. 61/393,103, filed on Oct. 14, 2010.

(51) Int. Cl.
| | |
|---|---|
| *A61K 9/00* | (2006.01) |
| *A61K 9/20* | (2006.01) |
| *A61K 31/444* | (2006.01) |
| *A61K 9/28* | (2006.01) |

(52) U.S. Cl.
CPC .......... *A61K 9/2054* (2013.01); *A61K 9/2009* (2013.01); *A61K 9/2013* (2013.01); *A61K 9/2018* (2013.01); *A61K 9/2027* (2013.01); *A61K 9/2059* (2013.01); *A61K 9/2095* (2013.01); *A61K 9/2813* (2013.01); *A61K 31/444* (2013.01)

(58) Field of Classification Search
CPC .. C07D 413/10; A61K 9/2059; A61K 9/2013; A61K 9/2018; A61K 9/2009; A61K 9/2027; A61K 9/2054; A61P 29/00; A61P 3/00

See application file for complete search history.

(56) References Cited

U.S. PATENT DOCUMENTS

| | | | | |
|---|---|---|---|---|
| 2005/0287209 | A1* | 12/2005 | Murphy | A61P 31/00 424/464 |
| 2008/0145425 | A1 | 6/2008 | Marija et al. | |
| 2009/0215780 | A1* | 8/2009 | Smith | A61P 3/10 514/237.5 |
| 2009/0247534 | A1* | 10/2009 | Serrano-Wu | A61P 9/04 514/252.03 |
| 2010/0221266 | A1* | 9/2010 | Gregory | C12N 15/113 424/174.1 |
| 2016/0374947 | A1 | 12/2016 | Wen et al. | |

FOREIGN PATENT DOCUMENTS

| | | | |
|---|---|---|---|
| WO | | 9717951 A1 | 5/1997 |
| WO | | 9749394 A2 | 12/1997 |
| WO | | 9952558 A1 | 10/1999 |
| WO | | 2007078726 A2 | 7/2007 |
| WO | | 2007103867 A2 | 9/2007 |
| WO | | 2007109713 A2 | 9/2007 |
| WO | | 2007126957 A2 | 11/2007 |
| WO | WO 2007/126957 | * | 11/2007 |
| WO | | 2008067257 A1 | 6/2008 |
| WO | | 2008134693 A1 | 11/2008 |
| WO | | 2010114801 A1 | 10/2010 |
| WO | | 2011123401 A1 | 10/2011 |

OTHER PUBLICATIONS

Aulton, Michael E. et al., Pharmaceutics: The Science of Dosage Form Design; Edinburgh; New York: Churchill Livingstone, 2002, pp. 181-and 248-252.

The European Commission; Title: Opinion on use of cross-linked sodium carboxymethl cellulose in solid dietary supplements, published Jan. 15, 1998. Downloaded from http://ec.europe.eu/food/fs/sc/sct/out02 on Dec. 27, 2014.

* cited by examiner

*Primary Examiner* — Ali Soroush
(74) *Attorney, Agent, or Firm* — Foley Hoag LLP

(57) ABSTRACT

The present invention relates to a pharmaceutical composition comprising
a) a therapeutically effective amount of a compound of formula (I), or a pharmaceutically acceptable salt thereof,
b) one or more, e.g. 1, 2 or 3, surfactants with lubricant properties;
c) one or more, e.g. 1, 2 or 3, dry binders with disintegrant properties;
d) one or more, e.g. 1, 2 or 3, fillers, and
e) one or more, e.g. 1, 2 or 3, disintegrants.

13 Claims, No Drawings

PHARMACEUTICAL COMPOSITIONS CONTAINING A DGAT1 INHIBITOR

RELATED APPLICATIONS

This application is a continuation of U.S. application Ser. No. 15/968,104, filed May 1, 2018, now allowed, which is a continuation of U.S. application Ser. No. 15/262,056, filed Sep. 12, 2016, which is a continuation of U.S. application Ser. No. 14/805,919, filed Jul. 22, 2015, which is a continuation of U.S. application Ser. No. 13/825,919, filed Mar. 25, 2013, which is a National Phase application of International Application No. PCT/US2011/056275, filed Oct. 14, 2011, which claims the benefit of and priority to U.S. Provisional Application No. 61/393,103, filed Oct. 14, 2010, the entire contents of each of which are incorporated herein by reference in their entireties.

FIELD OF THE INVENTION

The present invention relates to pharmaceutical compositions comprising (4-{4-[5-(6-trifluoromethyl-pyridin-3-ylamino)-pyridin-2-yl]-phenyl}-cyclohexyl)-acetic acid, or a pharmaceutically acceptable salt thereof, e.g., the sodium salt thereof, as the active ingredient in a suitable carrier. The present invention also relates to the processes for their preparation and to their use as medicaments.

BACKGROUND OF THE INVENTION

As disclosed in WO 2007/126957, a genus of compounds as DGAT1-inhibitors, Including, at Example 5-1, the compound (4-{4-[5-(6-trifluoromethyl-pyridin-3-ylamino)-pyridin-2-yl]-phenyl}-cyclohexyl)-acetic acid, having the structural formula (I):

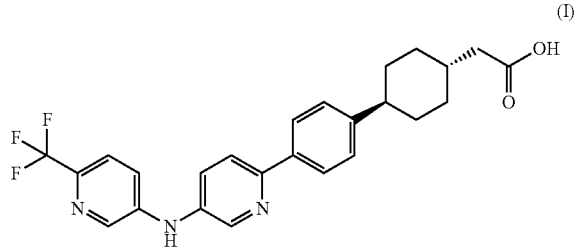 [SMILES: O=C(O)C[C@H]1CC[C@H](c2ccc(-c3ccc(Nc4ccc(C(F)(F)F)nc4)cn3)cc2)CC1]

(I)

and its sodium salt

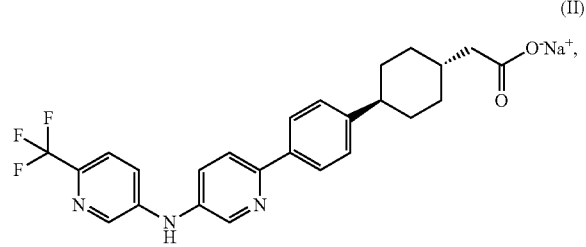

(II)

may be employed in the treatment of a condition or a disorder such as inflammatory conditions, obesity, diabetes and related metabolic disorders.

Administration of such pharmaceutical agents via the oral route is preferred to parenteral administration because it allows self-administration by patients whereas parenteral formulations have to be administered in most cases by a physician or paramedical personnel. It is also important that dosage units which are manufactured and given to a patient have a high degree of uniformity in the amount of drug substance among the individual dosage units. In addition, the formulation must have a good dissolution profile and an optimal in-vivo drug-release profile with minimal unit-to-unit variability.

However, the compound of formula (I), or a pharmaceutically acceptable salt thereof, in particular the sodium salt thereof, is a drug substance which is difficult to formulate due to its physicochemical properties. More particularly, the sodium salt of the compound of formula (I), depicted above as the compound of formula (II), is hygroscopic, poorly soluble and highly permeable, with a high moisture uptake at 95% relative humidity. It is also plate like, very fluffy, and sticky in nature. It also exhibits poor flow characteristics.

These characteristics of the drug substance make it particularly problematic to develop formulations comprising the compound of formula (II) which would be amenable to withstanding the compression forces required for a tablet form of the pharmaceutical composition with an adequate hardness window.

Furthermore, it is not trivial to make oral formulations of the compound of formula (II) in the form of tablets with the desirable required properties such as good flowability, compression behavior (e.g. no sticking during tablet compression), friability, and/or dissolution rate, in a reliable and robust way.

Accordingly, there is the need for a suitable and robust galenical formulation overcoming the above problems related to the properties of the compound of formula (II).

During the course of development, it has been found to be difficult to achieve such a formulation. The formulations of Example 1, for instance, were very sensitive to process parameters. It was found that compression at different hardnesses led to very different dissolution profiles. It was thus necessary to reduce the tablet to tablet variability of the drug release of the formulation, as this would have a major impact on the in-vivo availability of the drug. It was also necessary to develop a formulation which would be more robust to process parameters, and which would avoid one of the major problems associated with the compound of formula (II), i.e. its stickiness.

SUMMARY OF THE INVENTION

Surprisingly it has been found that the use of a combination of specific excipients enables the preparation of pharmaceutical compositions, in particular in the form of compressed tablets, overcoming the drawbacks identified above.

The invention thus provides a pharmaceutical composition of the compound of formula (I), or a pharmaceutically acceptable salt thereof, which exhibits one or more, e.g. 1, 2 or 3, of the following desirable characteristics;
  a dissolution profile which is suitable for the administration of the therapeutic agent,—a compression profile with a wide hardness window which still provides acceptable friability, hardness, disintegration time and dissolution;
  sufficient stability to achieve a reasonable shelf life;
  a relatively high drug loading, if desired, may easily be achieved.

The formulations of the present invention are also achievable via a robust manufacturing process; which gives good flowability, compactability, and which minimizes sticking problems and capping of tabletting mixtures on the rotary press. The process and the formulations are amenable to scale-up, with a reproducible performance.

Accordingly the present invention provides a pharmaceutical composition comprising
a) a therapeutically effective amount of a compound of formula (I), or a pharmaceutically acceptable salt thereof,
b) one or more, e.g. 1, 2 or 3, surfactants with lubricant properties;
c) one or more, e.g. 1, 2 or 3, dry binders with disintegrant properties;
d) one or more, e.g. 1, 2 or 3, fillers, and
e) one or more, e.g. 1, 2 or 3, disintegrants.

Preferred embodiments are as defined herein and in the subclaims.

DETAILED DESCRIPTION

The pharmaceutical composition in accordance with the present invention is, as defined in claim 1. The use of the specified excipients surprisingly overcomes the problems of formulating the compound of formula (I), or a pharmaceutically acceptable salt, in particular the sodium salt of formula (II), into a solid oral dosage form.

In particular, the present invention provides a composition which shows good physical and chemical stability during storage, which has a good dissolution profile, which is not sensitive to manufacturing parameters, and in which the unit to unit variation in drug release is minimized.

In particular, the present invention also provides a process which enables maximum drug load to be achieved and which is not sensitive to manufacturing parameters.

The present inventors have found that the presence of a surfactant which also has lubricant properties considerably reduces the sticking tendency of the formulation, as well as improving the dissolution and processing properties of the compositions of the present invention. Thus the pharmaceutical compositions of the present invention contain one or more, e.g. 1, 2 or 3, surfactants which have lubricant properties.

The surfactants to be employed in accordance in the present invention include, without limitation, sodium lauryl sulfate (SLS), stearic acid, palmitic acid, myristic acid, poloxamers and polyethylene glycols such as PEG 4000-8000, Tween series of surfactants, Brij series of surfactants (i.e., Brij 80), Triton X-100, and combinations thereof, preferably Sodium lauryl sulfate (SLS).

The surfactant or combination of surfactants may be employed in an amount ranging from about 0.1% to about 5%, preferably from about 0.5% to about 3%, e.g. 2%, by weight of the tablet (prior to any optional film coating). These percentages are based on the compound of the formula (I) and if a salt is used the percentages will be adapted accordingly.

Sticking issues during roller compaction and subsequent tabletting (at forces of 5 kN and less) are also overcome by the presence of a dry binder with lubricant properties. Moreover, the presence of such a binder gives more stable roller compaction roll-force readouts compared to those obtained in compositions without such a binder. Thus the pharmaceutical compositions of the present invention in addition contain one or more, e.g. 1, 2 or 3, binders with lubricant properties.

The dry binders to be employed in accordance in the present invention include, without limitation, polyethylene glycols (PEG), e.g., PEG 4000; pregelatinized starch; starch; chitosan; guar gum, microcrystalline cellulose; methyl cellulose; calcium carboxymethylcellulose; sodium carboxymethylcellulose, alginic acid and/or its sodium salt; hydroxypropylmethyl cellulose or hydroxypropyl cellulose, both preferably of medium to high viscosity, e.g., viscosity grades 3 or 6 cps, e.g. low substituted hydroxypropyl cellulose (L-HPC LH-21); and combinations thereof. A most preferred binder is low substituted hydroxypropyl cellulose (L-HPC LH-21).

The dry binder or combination of dry binders may be employed in an amount ranging from about 2% to about 20%, preferably from about 5% to about 15%, e.g. about 10% by weight of the tablet (prior to any optional film coating). These percentages are based on the compound of the formula (I) and if a salt is used the percentages will be adapted accordingly.

The fillers to be employed in accordance in the present invention include, without limitation, microcrystalline cellulose (e.g., cellulose MK GR and products available under the registered trade marks AVICEL, FILTRAK, HEWETEN or PHARMACEL, Vivapur, emcocel, tabulose), low-substituted hydroxypropyl cellulose, hydroxyethyl cellulose, hydroxypropyl methyl cellulose, Anhydrous Dicalcium Phosphate, Dicalcium Phosphate, lactose, Anhydrous Lactose, and combinations thereof.

Preferably the filler is microcrystalline cellulose, Anhydrous Dicalcium Phosphate and Anhydrous Lactose, or a mixture thereof. Combination of fillers may be used such as combinations of microcrystalline cellulose and Anhydrous Dicalcium Phosphate, and combinations of microcrystalline cellulose and lactose.

The filler or combination of fillers may be employed in an amount ranging from about 4% to about 85%, preferably from about 20% to about 85%, most preferably from about 50-80%, e.g, 50-65% or 70-80% by weight of the tablet (prior to any optional film coating). These percentages are based on the compound of the formula (I) and if a salt is used the percentages will be adapted accordingly.

When combinations of fillers are used, they may be used in a ratio of from 1:1 to 1:5, preferably 1:2 ratio.

In one embodiment, the filler is a combination of microcrystalline cellulose and another filler, e.g. Anhydrous Dicalcium Phosphate, or lactose, wherein the ratio of the microcrystalline cellulose to lactose, or of microcrystalline cellulose to anhydrous dicalcium phosphate is 1:2.

The disintegrants to be employed in the pharmaceutical compositions of the present invention can be extragranular or intragranular, or both. Examples of disintegrants to be employed in accordance in the present invention include, without limitation, carboxymethylcellulose calcium (CMC-Ca), carboxymethylcellulose sodium (CMC-Na) or croscarmellose sodium, e.g. AC-DI-SOL, Sodium Starch Glycollate (SSG); alginic acid, sodium alginate and guar gum; preferably croscarmellose sodium, e.g. AC-DI-SOL, cross-linked polyvinyl pyrrolidone (e.g. CROSPOVIDONE, POLYPLASDONE or KOLLIDON XL), Sodium Starch Glycollate (SSG).

A most preferred disintegrant is Sodium Starch Glycollate (SSG).

The disintegrant or combination of disintegrants may be employed in an amount ranging from about 0.5% to about 25%, preferably from about 1% to about 10%, most preferably from about 1% to about 6%, by weight of the tablet (prior to any optional film coating). In one embodiment, the disintegrant is present in an amount which is 2, 6 or 9% by weight of the tablet. These percentages are based on the compound of the formula (I) and if a salt is used the percentages will be adapted accordingly.

Lubricants may provide advantages in the formulation of a pharmaceutical composition when the drug substance is poorly water soluble and a compaction process, such as a roller compaction process, is used with drug loads as high as 25% w/w. Thus the pharmaceutical compositions of the present invention may in addition contain one or more, e.g. 1, 2 or 3, lubricants.

The lubricants to be employed in accordance in the present invention include, without limitation, magnesium stearate, aluminum or calcium silicate, stearic acid, cutina, PEG 4000-8000, talc and combinations thereof, preferably Sodium Stearyl Fumarate or magnesium stearate, more preferably Sodium Stearyl Fumarate.

The lubricant or lubricants may be employed in an amount ranging from about 0.1% to about 10%, preferably from about 0.5% to about 5%, e.g. 2-3%, by weight of the tablet (prior to any optional film coating). These percentages are based on the compound of the formula (I) and if a salt is used the percentages will be adapted accordingly.

The compound of formula (I), or a pharmaceutically acceptable salt, may be employed in an amount ranging from about 0.1% to about 50%, preferably from about 0.5% to about 30%, most preferably from about 1-30%, by weight of the pharmaceutical compositions (prior to any optional film coating). The compound of formula (I) may be present in 2, 10, 15, 20, 25 and 30% by weight of the pharmaceutical compositions. These percentages are based on the compound of the formula (I) and if a salt is used the percentages will be adapted accordingly.

Pharmaceutically acceptable additives suitable for use in the pharmaceutical compositions, in particular in the form of the tablets, according to the present invention include, without limitation, glidants, colorants, and combinations thereof. The amount of each additive in a pharmaceutical oral fixed dose combination may vary within ranges conventional in the art.

Suitable glidants include, without limitation, colloidal silicon dioxide (e.g., Aerosil 200), magnesium trisilicate, powdered cellulose, starch, talc and combinations thereof. When present, a glidant or glidants in the layer containing component a) may be employed in an amount ranging from about 00.05% to about 5%, preferably from about 0.1% to about 1%, more preferably from about 0.25% to about 1%, e.g. 0.25 or 0.5%, by weight of the tablet (prior to any optional film coating). These percentages are based on the compound of the formula (I) and if a salt is used the percentages will be adapted accordingly.

Various enumerated embodiments of the invention are described herein. It will be recognized that features specified in each embodiment may be combined with other specified features, wherein the specified features are as described in each embodiment, and also in the present specification, to provide further embodiments of the present invention.

In a first embodiment 1, the invention provides a pharmaceutical composition, as described in claim 1.

Embodiment 2: a pharmaceutical composition, according to embodiment 1, wherein the surfactant with lubricant properties is selected from, sodium lauryl sulfate (SLS), stearic acid, palmitic acid, myristic acid, poloxamers and polyethylene glycols such as PEG 4000-8000, Tween series of surfactants, Brij series of surfactants (i.e., Brij 80), Triton X-100, and combinations thereof, preferably Sodium lauryl sulfate (SLS).

Embodiment 3: a pharmaceutical composition, according to embodiment 1 or 2, wherein the dry binder is selected from polyethylene glycols (PEG), e.g., PEG 4000; pregelatinized starch; starch; chitosan; guar gum, microcrystalline cellulose; methyl cellulose; calcium carboxymethylcellulose; sodium carboxymethylcellulose, alginic acid and/or its sodium salt; hydroxypropylmethyl cellulose or hydroxypropyl cellulose, both preferably of medium to high viscosity, e.g., viscosity grades 3 or 6 cps, e.g. low substituted hydroxypropyl cellulose (L-HPC LH-21); and combinations thereof, most preferably, low substituted hydroxypropyl cellulose (L-HPC LH-21).

Embodiment 4; a pharmaceutical composition, according to any one of embodiments 1 to 3, wherein the filler is selected from microcrystalline cellulose (e.g., cellulose MK GR and products available under the registered trade marks AVICEL, FILTRAK, HEWETEN or PHARMACEL, Vivapur, emcocel, tabulose), low-substituted hydroxypropyl cellulose, hydroxyethyl cellulose, hydroxypropyl methyl cellulose, Anhydrous Dicalcium Phosphate, Dicalcium Phosphate, lactose, Anhydrous Lactose, and combinations thereof.

Embodiment 5; a pharmaceutical composition, according to any one of embodiments 1 to 4, wherein the disintegrant is selected from carboxymethylcellulose calcium (CMC-Ca), carboxymethylcellulose sodium (CMC-Na) or croscarmellose sodium, e.g. AC-DI-SOL, Sodium Starch Glycollate (SSG); alginic acid, sodium alginate and guar gum; preferably croscarmellose sodium, e.g. AC-DI-SOL, cross-linked polyvinyl pyrrolidone (e.g. CROSPOVIDONE, POLYPLASDONE or KOLLIDON XL), Sodium Starch Glycollate (SSG).

In other embodiments of the invention, the pharmaceutical compositions provided herein may contain in addition, lubricants, glidants, colorants, and combinations thereof, as detailed above.

In a preferred aspect, the amounts of each of the excipients, and the amount of the compound of formula (I), or a pharmaceutically acceptable salt thereof, are as described herein, and as described in the Examples.

Throughout the present application, the various terms are as defined below:

Hardness: The term "hardness" commonly also referred to as "breaking force" or "resistance to crushing" as used herein refers to the force required to cause a tablet to fail (i.e., break) in a specific plane.

The hardness is measured by standard methods known to the person skilled in the art, see the harmonized procedure set forth in the pharmacopeias USP <1217> and EP 2.9.8 and JP. If the tablet is too soft, it will not withstand handling during the subsequent processing, such as coating or packaging and shipping operations. Likewise, if the tablet is too hard, it may not disintegrate in the required period of time or meet the dissolution specification. A general principle for hardness testing is that the larger the tablet, the higher the hardness. It is thus a goal of the formulator to improve the compression/hardness profile so as to minimize the influence of hardness on disintegration time and dissolution, and to maximize the drug load.

Release profile: The term "release" as used herein refers to a process by which the pharmaceutical oral fixed dose combination is brought into contact with a fluid and the fluid transports the drug(s) outside the dosage form into the fluid that surrounds the dosage form. The combination of delivery rate and delivery duration exhibited by a given dosage form in a patient can be described as its in vivo release profile. The release/dissolution profiles of dosage forms may exhibit different rates and durations of release and may be continuous. Continuous release profiles include release profiles in which one or more, e.g. 1, 2 or 3, active ingredients are released continuously, either at a constant or variable rate. An adequate drug release profile for the pharmaceutical composition may be e.g. 80% within 45 minutes.

Disintegration: The term "disintegration" as used herein refers to a process where the pharmaceutical oral fixed dose combination, typically by means of a fluid, falls apart into separate particles and is dispersed. Disintegration is achieved when the solid oral dosage form is in a state in which any residue of the solid oral dosage form, except fragments of insoluble coating or capsule shell, if present, remaining on the screen of the test apparatus is a soft mass having no palpably firm core in accordance with USP<701>. The fluid for determining the disintegration property is water, such as tap water or deionized water. The disintegration time is measured by standard methods known to the person skilled in the art, see the harmonized procedure set forth in the pharmacopeias USP <701> and EP 2.9.1 and JP.

Dissolution rate: The term "dissolution" as used herein refers to a process by which a solid substance, here the active ingredients, is dispersed in molecular form in a medium. The dissolution rate of the active ingredients of the pharmaceutical oral fixed dose combination of the invention is defined by the amount of drug substance that goes in solution per unit time under standardized conditions of liquid/solid interface, temperature and solvent composition. The dissolution rate is measured by standard methods known to the person skilled in the art, see the harmonized procedure set forth in the pharmacopeias USP <711> and EP 2.9.3 and JP. For the purposes of this invention, the test is for measuring the dissolution of the individual active ingredients is performed following pharmacopeia USP <711> at pH 4.5 using a paddle stirring element at 75 rpm (rotations per minute). The dissolution medium is preferably a buffer, typically a phosphate buffer, especially one as described in the example "Dissolution Test". The molarity of the buffer is preferably 0.1 M.

An adequate dissolution profile for a slowly dissolving or poorly water soluble drug (BCS class 2) may mean for example, more than 80%, e.g. 85%, dissolution within 30, 45, or 60 minutes, see e.g. *Guidance for Industry: Dissolution Testing of Immediate Release Solid Oral Dosage Forms*, August 1997, p. 5.

The term "particulate" as used herein refers to a state of matter which is characterized by the presence of discrete particles, pellets, beads or granules irrespective of their size, shape or morphology. When a plurality of particulates is present, these are referred to as multiparticulates. Typically, the particulates have an average size of lower than about 3 mm, preferably between about 1 μm to 3 mm. By "average particle size" it is meant that at least 50% of the particulates have a particle size of less than about the given value, by weight. The particle size may be determined on the basis of the weight average particle size as measured by conventional particle size measuring techniques well known to those skilled in the art. Such techniques include, for example, sedimentation field flow fractionation, photon correlation spectroscopy, light scattering, and disk centrifugation.

The terms "effective amount" or "therapeutically effective amount" refers to the amount of the active ingredient or agent which halts or reduces the progress of the condition being treated or which otherwise completely or partly cures or acts palliatively on the condition.

The term "prophylactically effective amount" refers to the amount of the active ingredient or agent prevents the onset of the disease, condition or disorder.

The term "warm-blooded animal or patient" are used interchangeably herein and include, but are not limited to, humans, dogs, cats, horses, pigs, cows, monkeys, rabbits, mice and laboratory animals. In one embodiment, the mammals are humans.

The term "treatment" means the management and care of a patient for the purpose of preventing, combating or delaying progression of the disease, condition or disorder, preferably for the purpose of combating the disease, condition or disorder, and in particular it also prophylactic treatment.

The terms "prevention"/"preventing" are to be understood as meaning the prophylactic administration of a drug, such as a combined preparation or pharmaceutical composition, to healthy patients to prevent the outbreak of the disease, condition or disorder.

The terms "delay of progression"/"delaying progression" are to be understood as meaning the administration of a drug, such as a combined preparation or pharmaceutical composition, to patients being in a pre-stage of the disease, condition or disorder.

The terms "drug", "active substance", "active ingredient", "active agent" are to be understood as meaning a compound in free form or in the form of a pharmaceutically acceptable salt, in particular as specified herein.

Where the plural form is used for compounds, salts, excipients, pharmaceutical compositions, diseases, disorders and the like, this is intended to mean one or more, e.g. 1, 2 or 3, single compound(s), salt(s), excipients, pharmaceutical composition(s), disease(s), disorder(s) or the like, where the singular or the indefinite article ("a", "an") is used, this is intended to include the plural or the singular ("one").

In a further embodiment the present invention overcomes the drawbacks associated with formulating the drug substance and provides a specific process for preparing a pharmaceutical composition comprising the compound of the formula (I), or a pharmaceutically acceptable salt thereof.

The invention provides in another of its aspects a process of making a solid oral dosage form as hereinabove described. Such a solid oral dosage form may be produced by working up the final composition defined hereinabove in appropriate amounts, to form unit dosage forms.

In one embodiment, there is provided a process for preparing a pharmaceutical composition according to any one of the preceding claims comprising the steps of mixing compound of formula (I), or a pharmaceutically acceptable salt thereof, with at least one pharmaceutically acceptable excipient to form a blend; compacting, such as roller compacting, said blend; optionally mixing with further pharmaceutically acceptable excipients, and optionally compressing the final blend into a solid oral dosage form.

There is also provided a process of making the solid oral dosage forms as hereinabove described comprising the steps of
  (a) mixing the compound of the formula (I), or a pharmaceutically acceptable salt thereof with at least one pharmaceutically acceptable excipient to form a blend;
  (b) roller compacting, then milling said blend;
  (c) lubricating the resulting mixture, and
  (d) compressing the resulting mixture into a solid oral dosage form.

Quantities of ingredients, represented by percentage by weight of the pharmaceutical composition, used in each example are set forth in the respective tables located after the respective descriptions. A further embodiment of the present invention is a process for the manufacture of a tablet according to the present invention.

The pharmaceutical oral fixed compositions of the invention are tablets of low friability. Preferably the friability is not more than 0.8%. The friability is measured by standard methods known to the person skilled in the art, see the harmonized procedure set forth in the pharmacopeias USP <1216> and EP 2.9.7 and JP.

The pharmaceutical oral fixed compositions of the invention are tablets of suitable hardness (e.g. an average hardness ranging from about 30 N to about 110 N). Such an average hardness is determined prior to the application of any film coating on the pharmaceutical oral fixed dose combinations. In that regard, a preferred embodiment of this invention is directed to pharmaceutical oral compositions which are film-coated. Suitable film coatings are known and commercially available or can be made according to known methods. Typically the film coating material is a polymeric film coating material comprising materials such as hydroxypropylmethyl cellulose or polyvinyl alcohol, polyethylene glycol, lecithin, talc and colorant. Typically, a film coating material is applied in such an amount as to provide a film coating that ranges from about 1% to about 6% by weight of the film-coated tablet. A coating comprising polyvinyl alcohol and materials such as polyethylene glycol, talc, and colorants (such as Opadry AMB or Opadry II 85F) can be applied as a moisture barrier to provide additional moisture protection to prevent conversion of the active ingredient to other polymorphic forms. Sufficient moisture protection can also be achieved through various packaging, including but not limited to: heat-induction sealed HDPE bottles with or without desiccant, and blister packaging materials known in the industry to have low moisture vapor permeation rates (i.e. aluminum/aluminum, PVC/PCTFE (polyvinylchloride/polychlorotrifluoroethylene), ACLAR).

The invention provides a process for the preparation of pharmaceutical oral compositions as described herein above. Such pharmaceutical oral fixed dose combination may be produced by working up components as defined herein above in the appropriate amounts, to form unit pharmaceutical oral fixed dose combinations.

The pharmaceutical compositions are useful in treating or preventing a condition or disorder associated with DGAT1 activity. The conditions for which the instant invention is useful include, without limitation, a metabolic disorder such as obesity, diabetes, anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia, chlomicronemia, familial chylomicronemia, and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, and vascular stenosis; neoplastic diseases, such as solid tumors, skin cancer, melanoma, lymphoma, and endothelial cancers, for example, breast cancer, lung cancer, colorectal cancer, stomach cancer, other cancers of the gastrointestinal tract (for example, esophageal cancer and pancreatic cancer), prostate cancer, kidney cancer, liver cancer, bladder cancer, cervical cancer, uterine cancer, testicular cancer, and ovarian cancer; dermatological conditions, such as acne vulgaris. In yet another aspect, the pharmaceutical compositions are useful as an anorectic.

The present invention thus provides a method for treating or preventing a condition or disorder associated with DGAT1 activity, comprising administering to an animal, including a human patient, in need of such treatment a therapeutically effective amount of the pharmaceutical composition according to the present invention.

The present invention likewise provides the use of a pharmaceutical composition according to the present invention for the manufacture of a medicament for treating or preventing a condition or disorder associated with DGAT1 activity.

The present invention likewise provides a pharmaceutical composition according to the present invention for use in treating or preventing a condition or disorder associated with DGAT1 activity.

Ultimately, the exact dose of the active agent and the particular formulation to be administered depend on a number of factors, e.g., the condition to be treated, the desired duration of the treatment and the rate of release of the active agent. For example, the amount of the active agent required and the release rate thereof may be determined on the basis of known in vitro or in vivo techniques, determining how long a particular active agent concentration in the blood plasma remains at an acceptable level for a therapeutic effect.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way.

EXAMPLES

Methodology Example A: Dissolution Testing

The tablets of the Examples are tested for their dissolution in 900 ml of pH 6.8 phosphate buffer with paddles at 75 rpm.

The assembly consists of the following: a covered vessel made of glass or other inert, transparent material; a motor, and a paddle formed from a blade and shaft as the stirring element. The vessel is partially immersed in a suitable water bath of any convenient size or placed in a heating jacket. The water bath or heating jacket permits holding the temperature inside the vessels at 37±0.5° during the test and keeping the bath fluid in constant, smooth motion. No part of the assembly, including the environment in which the assembly is placed, contributes significant motion, agitation, or vibration beyond that due to the smoothly rotating stirring element. Apparatus that permits observation of the specimen and stirring element during the test is has the following dimensions and capacities: the height is 160 mm to 210 mm and its inside diameter is 98 mm to 106 mm. Its sides are flanged at the top. A fitted cover may be used to retard evaporation. The shaft is positioned so that its axis is not more than 2 mm at any point from the vertical axis of the vessel and rotates smoothly without significant wobble. The vertical center line of the blade passes through the axis of the shaft so that the bottom of the blade is flush with the bottom of the shaft. The design of the paddle is as shown in USP <711>, FIG. 2. The distance of 25±2 mm between the blade and the inside bottom of the vessel is maintained during the test. The metallic or suitably inert, rigid blade and shaft comprise a single entity. A suitable two-part detachable design may be used provided the assembly remains firmly engaged during the test. The paddle blade and shaft may be coated with a suitable inert coating. The dosage unit is allowed to sink to the bottom of the vessel before rotation of the blade is started. A small, loose piece of nonreactive material such as not more than a few turns of wire helix may be attached to dosage units that would otherwise float. Other validated sinker devices may be used. 1 L of a buffered aqueous solution, adjusted to pH 6.8±0.05 (0.05 M Phosphate buffer solution obtained by dissolving 6.805 g of potassium dihydrogen phosphate and 0.896 g of sodium hydroxide in and diluting to 1000 ml with water, and adjusting the pH to 6.80±0.05 using 0.2M sodium hydroxide or 1M phosphoric acid; referred hereinafter as "Dissolution Medium") is placed in the vessel of the apparatus, the apparatus is assembled, the Dissolution Medium is equilibrated to 37±0.5°, and the thermometer is removed. 1 dosage form (e.g. tablet or capsule) is placed on the apparatus, taking care to exclude air bubbles from the surface of the dosage-form unit, and immediately the apparatus is operated at a rate of 75+2 rpm. Within the time interval specified (e.g. 10, 20, 30, 45, 60, 90 and 120 min.), or at each of the times stated, a specimen (>1 ml) is withdrawn from a zone midway between the surface of the Dissolution Medium and the top of the rotating blade, not less than 1 cm from the vessel wall. [NOTE—the aliquots withdrawn for analysis are replaced with equal volumes of fresh Dissolution Mediums at 37° or, where it can be shown that replacement of the medium is not necessary, the volume change is corrected in the calculation. The vessel is kept covered for the duration of the test, and the temperature of the mixture under test at suitable times is verified.]. The specimen is filtered through a suitable filter, e.g. a 0.45 μm PVDF filter (Millipore) and the first mls (2 to 3 ml) of the filtrate are discarded. The analysis is performed by HPLC or UV detection. The test is repeated at least 6 times. with additional dosage form units.

Methodology Example B: Hardness Testing

A Schleuniger 8M Hardness tester was used to perform tablet hardness testing. Tablets were positioned on the instrument stage. Each tablet was oriented in the lengthwise same position according to distinguishing marks (when applicable). Testing was performed for 10 tablets from each batch and each compression force.

Example 1: Reference Example trans-(4-{4-[5-(6-Trifluoromethyl-pyridin-3-ylamino)-pyridin-2-yl]-phenyl}-cyclohexyl)-acetic acid, sodium salt along with Microcrystalline Cellulose (partial), and Crospovidone (intragranular) are mixed in a low shear mixer. The mixed contents, along with remaining Microcrystalline Cellulose are passed through an oscillating mill equipped with a suitable screen. The screened contents are mixed in a low shear mixer for a suitable amount of time. Colloidal silicon dioxide, screened through an appropriate screen is mixed with the blend from earlier step and the contents are mixed for a suitable amount of time. Magnesium Stearate, screened through a suitable screen size is added to the preblend and mixed for a suitable amount of time. The lubricated intragranular preblend is passed through a roller compaction system for densification at the optimized parameters for feed rate, roll speed and roll force. The ribbons from the process are collected and passed through an oscillating mill equipped with a suitable screen to get the desired milled material. The milled material is then mixed with extragranular prescreened Crospovidone and mixed in a low shear mixer for a suitable amount of time. To the mixture, prescreened Magnesium Stearate is added and mixed for a suitable amount of time. The final blend is then compressed to the desired tablet weight to achieve the optimized thickness, hardness and disintegration time.

Example 1.A Uncoated Tablet Comprising a DGAT1 Inhibitor, (5 mg of Active Ingredient, Based on Free Acid of Compound 1)

| Ingredients | mg/tab |
|---|---|
| trans-(4-{4-[5-(6-Trifluoromethyl-pyridin-3-ylamino)-pyridin-2-yl]-phenyl}-cyclohexyl)-acetic acid, sodium salt | 5.26 |
| Microcrystalline Cellulose | 86.24 |
| Crospovidone | 7.0 |
| Colloidal silicon dioxide | 0.5 |
| Magnesium Stearate | 1.0 |
| Total weight | 100 mg |

Example 1.B Uncoated Tablet Comprising a DGAT1 Inhibitor, (10 mg of Active Ingredient, Based on Free Acid of Compound 1)

| Ingredients | mg/tab |
|---|---|
| trans-(4-{4-[5-(6-Trifluoromethyl-pyridin-3-ylamino)-pyridin-2-yl]-phenyl}-cyclohexyl)-acetic acid, sodium salt | 10.51 |
| Microcrystalline Cellulose | 172.49 |
| Crospovidone | 14.0 |
| Colloidal silicon dioxide | 1.0 |
| Magnesium Stearate | 1.0 |
| Total weight | 100 mg |

The Table below shows the dissolution of tablets of Example 1.A which are compressed at two different hardness i.e. 6 kN and 12 kN. The dissolution for the batches was performed using USP-2 Paddle/0.4% CTAB/pH 6.8 buffer/50 rpm.

TABLE

Dissolution summary of Example 1.A (at two hardness levels)

| | % compound of formulat (II)released (% w/w) at the following time points (in minutes) | | | | |
|---|---|---|---|---|---|
| Compression hardness | 10 min | 20 min | 30 min | 45 min | 60 min |
| 6 kN | 65 | 82 | 91 | 101 | 103 |
| 12 kN | 48 | 77 | 82 | 86 | 89 |

Example 2: Effect of Surfactant with Lubricant Properties

Method for Preparing a Pharmaceutical Composition:

Microcrystalline cellulose (Avicel), surfactant (sodium lauryl sulfate), disintegrant (Internal), and glidant (Aerosil 200) (Internal) are added to the therapeutic agent. The mixture is sieved and blended prior to lubrication. The lubricant (Internal), is then added to the bin blender and blended for an appropriate amount of time. The mixture is roller compacted using a roller compactor, and then milled.

Disintegrant (External), and glidant (Aerosil 200) (External) are added to the mixture and bin blended. Thereafter, the obtained mixture is blended with lubricant (external excipient), sieved in a bin blender. The obtained final mixture is then compressed into a tablet weighing about 100 mg.

The table below shows the effect of a surfactant with lubricant properties. The following Table shows two formulations, one with and the other without Sodium Lauryl Sulfate.

TABLE

Effect of surfactant with lubricant properties

| | Batch Number | |
|---|---|---|
| | Example 2A | Example 2B |
| | Strength | |
| | 25 mg mg/tablet | 25 mg mg/tablet |
| Materials | | |
| Compound of formula (II) | 26.28 | 26.28 |
| Sodium Lauryl Sulfate | — | 2 |
| Avicel PH 102 | 18.22 | 18.22 |
| Anhydrous Lactose | 36 | 36 |
| Sodium Starch Glycollate (Internal) | 3 | 3 |
| L-HPC LH 21 | 10 | 10 |
| Aerosil 200 (Internal) | 0.25 | 0.25 |
| Sodium Stearyl Fumarate (Internal) | 0.5 | 0.5 |
| Sodium Starch Glycollate (External) | 3 | 3 |
| Aerosil 200 (External) | 0.25 | 0.25 |
| Sodium Stearyl Fumarate (External) | 0.5 | 0.5 |
| Total weight (mg) | 100 | 100 |
| Tablet properties | | |
| Tooling | 6 mm round | 6 mm round |
| Mean weight (mg) | 99.4 | 100.5 |
| Compression force (kN) | 4.1 | 4.9 |
| Mean hardness (N) | 64.2 | 64.2 |

L- HPC LH 21: low substituted hydroxypropyl cellulose

The dissolution profiles of the above formulations are given below.

TABLE

Dissolution summary of Example 2 (with and without surfactant)

| | % compound released (% w/w) at the following time points (in minutes) | | | | |
|---|---|---|---|---|---|
| Sample | 10 | 20 | 30 | 45 | 60 |
| Without surfactant | 30 | 66 | 87 | 93 | 95 |
| With 2% surfactant | 50 | 84 | 92 | 94 | 94 |

The dissolution comparison clearly indicates the faster rate of dissolution at the initial two time points for the formulation with 2% w/w of SLS. Moreover, during the processing of the batch containing SLS, it was observed that the sticking tendency to the rolls of the compactor was also significantly reduced. Hence the advantages from the dissolution and processing standpoint made it crucial to include a surfactant with lubricant properties in the formulation.

Example 3: Effect of Dry Binder with Disintegrant Properties

The effect of a dry binder with disintegrant properties can be evaluated as follows. In Example 3B, the non-inclusion of L-HPC LH-21 was compensated by a similar amount of Avicel PH-102 in the external phase.

| | Batch Number | |
|---|---|---|
| | Example 3A | Example 3B |
| | Strength | |
| | 25 mg Mg/tablet | 25 mg Mg/tablet |
| Materials | | |
| Compound of formula (II) | 26.28 | 26.28 |
| Sodium Lauryl Sulfate | 2 | 2 |
| Avicel PH 102 (Internal) | 16.72 | 16.72 |
| Anhydrous Lactose | 36 | 36 |
| Sodium Starch Glycollate (Internal) | 3 | 3 |
| L-HPC LH 21 | 10 | — |
| Aerosil 200 (Internal) | 0.25 | 0.25 |
| Sodium Stearyl Fumarate (Internal) | 1 | 1 |
| Avicel PH 102 (External) | — | 10 |
| Sodium Starch Glycollate (External) | 3 | 3 |
| Aerosil 200 (External) | 0.25 | 0.25 |
| Sodium Stearyl Fumarate (External) | 1.5 | 1.5 |
| Total weight (mg) | 100 | 100 |
| Tablet properties | | |
| Tooling | 6 mm standard round, | 6 mm standard round, |
| Mean weight (mg) | 102.4 | 101.0 |
| Compression force (kN) | 8.4 | 8.1 |
| Mean hardness (N) | 89.0 | 89.2 |
| % friability (500 rotations) | 0.06 | 0.65 |

L- HPC LH 21: low substituted hydroxypropyl cellulose

The Table below gives details of the dissolution profile of the above formulations and the low and high hardness samples from each of the batches.

| | % compound released (% w/w) at the following time points (in minutes) | | | | |
|---|---|---|---|---|---|
| Sample | 10 | 20 | 30 | 45 | 60 |
| Ex. 3A (35 N hardness) | 56 | 95 | 95 | 96 | 96 |
| Ex. 3A (89 N hardness) | 44 | 75 | 90 | 94 | 96 |
| Ex. 3B (38 N hardness) | 51 | 90 | 97 | 98 | 98 |
| Ex. 3B (90 N hardness) | 40 | 73 | 90 | 96 | 98 |

The above table shows there is no clear difference between the dissolution profiles in terms of induced formulation changes with respect to the presence and absence of L-HPC LH-21. However from a processing standpoint, batch Example 3B encountered sticking issues during roller compaction and subsequent tabletting (at forces of 5 kN and less). Moreover, it was observed that for the formulation without the dry binder under consideration, roller compaction roll-force readouts were less stable compared to that of the formulation Example 3A.

The friability of a formulation containing a dry binder with lubricant properties was lower.

Therefore a dry binder with lubricant properties is an essential component of the formulations of the present invention.

Example 4: Effect of Filler Type

|  | Example 4A | Example 4B |
|---|---|---|
|  | Strength | |
|  | 25 mg mg/tablet | 25 mg mg/tablet |
| Materials | | |
| Compound of formula (II) | 26.28 | 26.28 |
| Sodium Lauryl Sulfate | 2 | 2 |
| Avicel PH 102 | 18.22 | 18.22 |
| Dicalcium Phosphate Anydrous | 36 | — |
| Anhydrous Lactose | — | 36 |
| Sodium Starch Glycollate (Internal) | 3 | 3 |
| L-HPC LH 21 | 10 | 10 |
| Aerosil 200 (Internal) | 0.25 | 0.25 |
| Sodium Stearyl Fumarate (Internal) | 0.5 | 0.5 |
| Sodium Starch Glycollate (External) | 3 | 3 |
| Aerosil 200 (External) | 0.25 | 0.25 |
| Sodium Stearyl Fumarate (External) | 0.5 | 0.5 |
| Total weight (mg) | 100 | 100 |
| Tablet properties | | |
| Tooling | 6 mm round | 6 mm round |
| Compression force (kN) | 9.59 | 4.9 |
| Mean hardness (N) | 86.6 | 64.2 |
| % friability (500 rotations) | 0.29% | NA |

Avicel PH 102: Microcrystalline cellulose (MCC)
Anhydrous Dicalcium Phosphate: DCP The dissolution profile of Example 4A and 4B are given in the Table below. The dissolution comparison from the Table clearly indicates that the core tablets from batch from containing MCC:DCP in a 1:2 ratio exhibited a slower profile than the batch containing MCC: Anhydrous Lactose in a 1:2 ratio.

|  | % compound released (% w/w) at the following time points (in minutes) | | | | |
|---|---|---|---|---|---|
| Sample | 10 | 20 | 30 | 45 | 60 |
| Ex. 4A (25N hardness) | 33 | 51 | 60 | 68 | 80 |
| Ex. 4B (47N hardness) | 57 | 92 | 94 | 95 | 97 |
| Ex. 4B (99N hardness) | 46 | 78 | 92 | 94 | 97 |

Example 5, Uncoated 25 mg Variants with Different Types of Disintegrants

The therapeutic agent in these examples is the compound of formula (II). The table below shows the formulation for Examples 5A, 5B and 5C having 25 mg of therapeutic agent—the 25 mg refers to the amount of the compound of formula (I). Examples 5A, 5B and 5C provide possible embodiments of a tablet dosage form using various disintegrants.

Microcrystalline cellulose (Avicel). sodium lauryl sulfate, disintegrant (Internal), and Aerosil 200 (Internal) are added to the therapeutic agent. The mixture is sieved and blended prior to lubrication. The Sodium Stearyl Fumarate (Internal), is then added to the bin blender and blended for an appropriate amount of time. The mixture is roller compacted using a roller compactor, and then milled. Disintegrant (External), and Aerosil 200 (External) are added to the mixture and bin blended. Thereafter, the obtained mixture is blended with Sodium Stearyl Fumarate (external excipient), sieved in a bin blender. The obtained final mixture is then compressed into a tablet weighing about 100 mg. The dissolution data of these examples at pH 6.8 are shown in the Table below.

TABLE

Uncoated 25 mg variants with different types of disintegrants

|  | Batch Number | | |
|---|---|---|---|
|  | Example 5.1 | Example 5.2 | Example 5.3 |
|  | Strength | | |
|  | 25 mg mg/tablet | 25 mg mg/tablet | 25 mg mg/tablet |
| Materials | | | |
| Therapeutic agent | 26.28 | 26.28 | 26.28 |
| Sodium Lauryl Sulfate | 2 | 2 | 2 |
| Avicel PH 102 | 18.22 | 18.22 | 18.22 |
| Anhydrous Lactose | 36 | 36 | 36 |
| Disintegrant (internal) | 3 (SSG) | 3 (PVP XL) | 3 (Ac-Di-Sol) |
| L-HPC LH 21 | 1 | 10 | 10 |
| Aerosil 200 (Internal) | 0.25 | 0.25 | 0.25 |
| Sodium Stearyl Fumarate (Internal) | 0.5 | 0.5 | 0.5 |
| Disintegrant (External) | 3 (SSG) | 3 (PVP XL) | 3 (Ac-Di-Sol) |
| Aerosil 200 (External) | 0.25 | 0.25 | 0.25 |
| Sodium Stearyl Fumarate (External) | 0.5 | 0.5 | 0.5 |
| Total weight (mg) | 100 | 100 | 100 |
| Tablet properties | | | |
| Tooling | 6 mm round | 6 mm round | 6 mm round |
| Mean weight (mg) | 100.1 | 102.3 | 99.2 |
| Compression force (kN) | 6.1 | 6.3 | 6.1 |
| Mean hardness (N) | 76.6 | 84.2 | 82.4 |
| % friability (500 rotations) | 0.41 | 0.08 | 0.75 |

SSG = Sodium Starch Glycollate;
PVP- XL: Cross linked polyvinyl pyrollidone
Ac-di-sol: Crosscarmellose Sodium;
L- HPC 21: low substituted hydroxypropyl cellulose

TABLE

Dissolution profiles for Examples 5.1-5.3.
Dissolution medium: 900 ml pH 6.8 Phosphate + 0.05% CTAB;
Paddle at 75 rpm; HPLC method; rapid stir 45 to 60 min.

|  |  | Time (min) 10 | 20 | 30 | 45 | 60 |
|---|---|---|---|---|---|---|
| % release of compound of formula (II) | Example 5.1 (SSG) (2.8 kN) | 36.3 | 73.3 | 83.4 | 90.3 | 93.8 |
| | Example 5.1 (SSG) (8.3 kN) | 30.0 | 58.2 | 78.5 | 88.0 | 92.9 |
| | Example 5.2 (PVP-XL) (2.8 kN) | 27.9 | 65.0 | 84.3 | 92.0 | 94.0 |
| | Example 5.2 (PVP-XL) (8.0 kN) | 21.9 | 51.2 | 74.5 | 87.9 | 93.1 |
| | Example 5.3 (Ac-di-sol) (2.5 kN) | 46.3 | 78.7 | 84.3 | 89.1 | 91.2 |

TABLE-continued

Dissolution profiles for Examples 5.1-5.3.
Dissolution medium: 900 ml pH 6.8 Phosphate + 0.05% CTAB;
Paddle at 75 rpm; HPLC method; rapid stir 45 to 60 min.

| Time (min) | 10 | 20 | 30 | 45 | 60 |
|---|---|---|---|---|---|
| Example 5.3 (Ac-di-sol) (8.0 kN) | 38.0 | 67.2 | 81.9 | 85.6 | 90.9 |

It can be seen from the above table that core tablets formulated with Cross linked polyvinyl pyrollidone (PVP-XL) show a slower release compared to the Sodium Starch Glycollate (SSG), and Croscarmellose Sodium (Ac-Di-Sol) based formulations. In addition, it was found that Cross linked polyvinyl pyrollidone (PVP-XL) was incompatible with the drug substance due to the presence of residual formaldehyde. Formulations containing Croscarmellose Sodium (Ac-Di-Sol) were also found to turn to yellow when prepared and exposed to 50° C. dry as well as 50° C./75% residual humidity for 4 weeks.

Thus, a most preferred disintegrant is sodium starch glycollate, which also gives a good friability level.

Example 6, 25 mg Tablet

The therapeutic agent in these examples is the compound of formula (II). The table below shows the formulation for Examples 6.1 to 6.4 having 25 mg of therapeutic agent—the 25 mg refers to the amount of the compound of formula (I). Tablets for examples 6.1 to 6.4 were made by the same process as described in example 2.

TABLE

Uncoated 25 mg variants with different levels of disintegrant

|  | Batch Number | | | |
|---|---|---|---|---|
|  | Example 6.1 | Example 6.2 | Example 6.3 | Example 6.4 |
|  | Strength | | | |
|  | 25 mg mg/tablet | 25 mg mg/tablet | 25 mg mg/tablet | 25 mg mg/tablet |
| Materials | | | | |
| Therapeutic agent | 26.28 | 26.28 | 26.28 | 26.28 |
| Sodium Lauryl Sulfate | 2 | 2 | 2 | 2 |
| Avicel PH 102 | 19.57 | 18.72 | 16.72 | 15.72 |
| Anhydrous Lactose | 39.15 | 38 | 36 | 34 |
| Sodium Starch Glycollate (Internal) | 0 | 1 | 3 | 4.5 |
| L-HPC LH 21 | 10 | 10 | 10 | 10 |
| Aerosil 200 (Internal) | 0.25 | 0.25 | 0.25 | 0.25 |
| Sodium Stearyl Fumarate (Internal) | 1 | 1 | 1 | 1 |
| Sodium Starch Glycollate (External) | 0 | 1 | 3 | 4.5 |
| Aerosil 200 (External) | 0.25 | 0.25 | 0.25 | 0.25 |
| Sodium Stearyl Fumarate (External) | 1.5 | 1.5 | 1.5 | 1.5 |
| Total weight (mg) | 100 | 100 | 100 | 100 |
| Tablet properties | | | | |
| Tooling | 6 mm round | 6 mm round | 6 mm round | 6 mm round |
| Mean weight (mg) | — | 101.6 | 101.8 | 100.5 |
| Compression force (kN) | — | 6.0 | 6.0 | 6.1 |
| Mean hardness (N) | 86.7 | 78.8 | 75.8 | 82.4 |
| % friability (500 rotations) |  | 0.29 | 0.12 | 0.18 |

The in vitro dissolution rate data of Examples 6.1 to 6.4 are given in Table below.

TABLE

In vitro dissolution rate of Examples 6.1 to 6.4
Dissolution medium: 900 ml pH 6.8 Phosphate + 0.05%
CTAB (cetyltrimethyl ammonium bromide);
Paddle at 75 rpm; HPLC method; rapid stir 45 to 60 min.

| | Time (min) | 10 | 20 | 30 | 45 | 60 |
|---|---|---|---|---|---|---|
| % release of compound of formula (II) | Example 6.1: 0% SSG (3.0 kN) | 21.15 | 50.56 | 74.45 | 89.81 | 93.21 |
| | Example 6.1: 0% SSG (7.9 kN) | 32.66 | 77.01 | 91.90 | 93.40 | 94.28 |
| | Example 6.2: 2% SSG (3.4 kN) | 30.78 | 62.63 | 81.91 | 94.82 | 96.07 |
| | Example 6.2: 2% SSG (8.0 kN) | 40.47 | 80.34 | 93.95 | 96.07 | 97.35 |
| | Example 6.3: 6% SSG (3.1 kN) | 44.29 | 75.02 | 89.89 | 94.23 | 96.04 |
| | Example 6.3: 6% SSG (8.4 kN) | 56.42 | 95.26 | 95.04 | 96.34 | 96.48 |
| | Example 6.4: 9% SSG (3.0 kN) | 39.55 | 74.20 | 92.06 | 96.12 | 98.03 |
| | Example 6: 9% SSG (8.3 kN) | 52.35 | 89.48 | 93.43 | 97.17 | 98.85 |

The dissolution profiles show a clear rank order in terms of level of disintegrant and the rate of dissolution up to 6% level. There was no significant difference in the release rates between 6% and 9%. Greater than 90% of the therapeutic agent is released from Examples with a disintegrant. Disintegrants usually decrease the compressibility of the formulation and higher levels will lead to decreased tablet hardness and/or friability problems. Thus, a fine balance must be struck between the amount of disintegrant and other properties of the formulation.

The disintegrant is distributed equally between the internal and external components. E.g. 6% is distributed as 3% internal and 3% external components, respectively, and 2% is distributed as 1% internal and 1% external components, respectively Example 7, 2 mg Tablet The therapeutic agent in this example is the compound of formula (II). Tables below show the formulation for Example 7 having 2 mg of therapeutic agent; the 2 mg refers to the amount of the compound of formula (I).

| Materials | Strength 2 mg mg/tablet |
| --- | --- |
| Therapeutic agent | 2.10 |
| Sodium Lauryl Sulfate | 2 |
| Avicel PH 102 (Internal) | 25.63 |
| Anhydrous Lactose DT | 51.27 |
| Sodium Starch Glycollate (Internal) | 3 |
| L-HPC LH 21 | 10 |
| Aerosil 200 (Internal) | 0.25 |
| Sodium Stearyl Fumarate (Internal) | 1 |
| Sodium Starch Glycollate (External) | 3 |
| Aerosil 200 (External) | 0.25 |
| Sodium Stearyl Fumarate (External) | 1.5 |
| Total weight (mg) | 100 |
| Tablet properties | |
| Tooling | 6 mm standard round |
| Compression force (kN) | 8.0 |
| Mean hardness (N) | 34.0 |
| % friability (500 rotations) | 0.66 (6 KN, 23.6N hardness) |
| DT mins (with disc.) | 4.8 |

Example 8: 20 mg Strength Uncoated Tablets with 6% Disintegrant, and 2% Disintegrant The therapeutic agent in these examples is the compound of formula (II). Table below shows the formulation for Examples 8.1 and 8.2 having 20 mg of therapeutic agent—the 20 mg refers to the amount of the compound of formula (I).

| | Batch Number | |
| --- | --- | --- |
| | Example 8.1 | Example 8.2 |
| | Strength | |
| Materials | 20 mg mg/tablet | 20 mg mg/tablet |
| Therapeutic agent | 21.02 | 21.02 |
| Sodium Lauryl Sulfate | 2 | 2 |
| Avicel PH 102 | 19.33 | 20.67 |
| Anhydrous Lactose | 38.67 | 41.33 |
| Sodium Starch Glycollate (Internal) | 3 | 1 |
| L-HPC LH 21 | 10 | 10 |
| Aerosil 200 (Internal) | 0.25 | 0.25 |
| Sodium Stearyl Fumarate (Internal) | 1.0 | 1.0 |
| Sodium Starch Glycollate (External) | 3 | 1 |
| Aerosil 200 (External) | 0.25 | 0.25 |
| Sodium Stearyl Fumarate (External) | 1.5 | 1.5 |
| Total weight (mg) | 100 | 100 |

Example 9: Technical Stability of Examples

Technical stability data, summarized in the tables below show that the tablets of the present invention have good stability even without desiccant. Tablet were packaged in 90 cc HPDE bottle with heat-induction seal.

TABLE

| Chemical data: 25 mg, 2% disintegrant, tablet- Example 6.2 | | | |
| --- | --- | --- | --- |
| Storage conditions | | Assay of active ingredient [% Compound of formula (II)] | Degradation products |
| Initial analysis | | 98.6 | None above 0.05% |
| 25° C./60% RH | 1 months | 98.1 | None above 0.05% |
| | 9 months | 97.3 | None above 0.05% |
| 40° C./75% RH | 1 months | 98.5 | None above 0.05% |
| | 3 months | 96.3 | None above 0.05% |

RH = relative humidity

TABLE

| Physical data: 25 mg, 2% disintegrant, tablet- Example 6.2 | | | | | |
| --- | --- | --- | --- | --- | --- |
| | | | Dissolution after 45 min. [%] | | Water content |
| Storage conditions | | Appearance | Average (n) | [min, max] | [%] |
| Initial analysis | | Complies* | 93 (12) | [91, 98] | 3.1 |
| 25° C./60% RH | 1 month | No change | 95 (6) | [93, 97] | 4.3 |
| 40° C./75% RH | 1 month | No change | 94 (6) | [92, 96] | 4.1 |
| | 3 months | No change | 96 (6) | [95, 98] | 4.4 |
| | 6 months | No change | 91 (6) | [89, 93] | — |

RH = relative humidity

TABLE

Chemical data: 25 mg, 6% disintegrant, tablet- Example 6.3

| Storage conditions | | Assay of active ingredient [% Compound of formula (II)] | Degradation products |
|---|---|---|---|
| Initial analysis | | 99.5 | None above 0.05% |
| 25° C./60% RH | 1 months | 99.0 | None above 0.05% |
| | 6 months | 98.3 | None above 0.05% |
| | 9 months | 97.3 | None above 0.05% |
| 40° C./75% RH | 1 months | 99.2 | None above 0.05% |
| | 3 months | 97.6 | None above 0.05% |
| | 6 months | 99.0 | None above 0.05% |

RH = relative humidity

TABLE

Physical data: 25 mg, 6% disintegrant, tablet- Example 6.3

| Storage conditions | | Appearance | Dissolution after 45 min. [%] Average (n) | [min, max] | Water content [%] |
|---|---|---|---|---|---|
| Initial analysis | | Complies* | 95 (12) | [93, 98] | 3.3 |
| 25° C./60% RH | 1 month | No change | 93 (6) | [90, 95] | 4.1 |
| | 6 months | No change | 93 (6) | [92, 94] | 3.7 |
| 40° C./75% RH | 1 month | No change | 95 (6) | [91, 99] | 4.4 |
| | 3 month | No change | 98 (6) | [94, 103] | 4.7 |
| | 6 months | No change | 95 (6) | [92, 97] | 5.1 |

RH = relative humidity

Example 10: Bioavailability of Tablet Formulations

A single center, randomized, open-label, single dose, parallel-group study is carried out to assess the relative bioavailability of the therapeutic agent following oral administration of a single dose of the compound of formula (II) as tablet (20 mg) formulations administered to healthy subjects under fasting or fed conditions (standard FDA breakfast). A total of 120 subjects are enrolled and equally distributed to 5 treatment arms (24 subjects/treatment arm, in a 1:1:1:1:1 ratio).

T1: one 20 mg tablet (Example 8.1) under fasting condition

T2: one 20 mg tablet (Example 8.2) under fasting condition

T3: two 10 mg tablets (Reference Example 1.B) under fasting condition

T4: one 20 mg tablet (Example 8.1) under fed condition

T5: one 20 mg tablet (Example 8.2) under fed condition

All subjects participate in a screening period of up to 20-days (Day −21 to −2), a baseline period (Day −1), a single-dose treatment period followed by 36 days of out-patient follow-up visits, and an end-of-study evaluation (Day 36). Subjects who comply with the inclusion/exclusion criteria at screening are admitted for baseline evaluations on the day before dosing. All baseline safety evaluation results must be available prior to dosing.

Serial pharmacokinetic (PK) blood samples are collected on Days 1 through 36 following study drug administration to determine the PK profile of different formulations of the present invention.

Safety assessments include physical examinations, ECGs, vital signs, standard clinical laboratory evaluations hematology, blood chemistry, urinalysis, adverse event and serious adverse event monitoring.

Pharmacokinetic Assessments:

PK blood collection (3 mL in EDTA tubes (plasma)): Pre-dose, 1, 2, 4, 6, 8, 10, 12, 24, 48, 72, 96, 120, 144, 168, 240, 312, 408, 504, 672, 840 hours post-dose.

The exact time of blood collection is recorded on the eCRF.

Analytes, media and methods: compound of formula (II) in plasma by validated LC-MS/MS method.

PK parameters of compound of formula (II) (to be determined for each of the tablet formulation): Cmax, Tmax, AUC0-last, AUC0-inf, t½, CL/F, and Vd/F PK evaluations: Descriptive statistics of all calculated PK parameters are provided.

TABLE

Summary of pharmacokinetic parameters following single oral administration of 20 mg of the therapeutic agent as Example 8.1, Example 8.2 or Reference Example 1.B tablet under fasted condition or Example 8.1, Example 8.2 under fed condition in healthy subjects

| PK arameter | | Example 8.1 fasted | Example 8.2 fasted | Reference Example 1.B tablet | Example 8.1 fed | Example 8.2 fed |
|---|---|---|---|---|---|---|
| Tmax (hr)[a] | N | 24 | 24 | 24 | 23 | 22 |
| | Median | 23.5 | 17.0 | 36.0 | 12.0 | 12.0 |
| | (min, max) | (9.95, 144) | (4.00, 120) | (4.00, 144) | (2.00, 119) | (4.00, 48.0) |
| Cmax | N | 24 | 24 | 24 | 23 | 22 |
| (ng/mL)[a] | Mean ± SD | 141 ± 85.5 | 161 ± 132 | 131 ± 84.0 | 260 ± 235 | 219 ± 190 |
| | (% CV) | (60.5) | (81.7) | (64.3) | (90.4) | (86.7) |
| T(½) (hr)[a, b] | N | 23 | 24 | 23 | 22 | 22 |
| | Mean ± SD | 136 ± 28.2 | 153 ± 59.2 | 140 ± 45.1 | 164 ± 95.0 | 139 ± 34.4 |
| | (% CV) | (20.8) | (38.6) | (32.3) | (57.8) | (24.7) |

TABLE-continued

Summary of pharmacokinetic parameters following single oral administration of 20 mg of the therapeutic agent as Example 8.1, Example 8.2 or Reference Example 1.B tablet under fasted condition or Example 8.1, Example 8.2 under fed condition in healthy subjects

| PK arameter | | Example 8.1 fasted | Example 8.2 fasted | Reference Example 1.B tablet | Example 8.1 fed | Example 8.2 fed |
|---|---|---|---|---|---|---|
| AUClast (hr*ng/mL)[a] | N | 24 | 24 | 24 | 23 | 22 |
| | Mean ± SD | 18400 ± 11300 | 22100 ± 14500 | 20300 ± 13000 | 33100 ± 23200 | 29700 ± 16800 |
| | (% CV) | (61.0) | (65.7) | (64.3) | (70.1) | (56.4) |
| AUCinf (hr*ng/mL)[a, b] | N | 23 | 24 | 23 | 23 | 22 |
| | Mean ± SD | 19400 ± 11400 | 23100 ± 15500 | 21800 ± 13800 | 34000 ± 23300 | 30300 ± 16900 |
| | (% CV) | (58.7) | (67.1) | (63.3) | (68.6) | (55.7) |
| CL/F (mL/hr)[a, b] | N | 23 | 24 | 23 | 23 | 22 |
| | Mean ± SD | 1310 ± 572 | 1330 ± 882 | 1260 ± 716 | 812 ± 392 | 880 ± 536 |
| | (% CV) | (43.6) | (66.2) | (57.0) | (48.3) | (61.0) |
| Vz/F (mL)[a, b] | N | 23 | 24 | 23 | 23 | 22 |
| | Mean ± SD | 252000 ± 113000 | 269000 ± 169000 | 254000 ± 192000 | 194000 ± 170000 | 172000 ± 93000 |
| | (% CV) | (45.1) | (62.8) | (75.6) | (87.9) | (54.2) |

[a] Values for subjects who vomited within 2 × Tmax were not included in this table
[b] Values for subjects whose Rsq adjusted <0.75 and/or whose AUC % extrapolated >25 were not included in this table Following oral administration of 20 mg tablets of the compound of formula (II) as Example 8.1 and Example 8.2 or Reference Example 1.B to fasted healthy subjects, the plasma concentration-time profiles were nearly super-imposable, especially at the latter time points, indicating similar rates and extent of absorption and elimination for the three formulations. There were small differences in the pharmacokinetic parameters (Cmax, AUClast and AUCinf) of the three formulations. However, these differences were not statistically significant.

Examples 8.1 and 8.2 are thus similar to Reference Example 1.B in terms of the rate and extent of absorption of the therapeutic agent.

The invention thus provides a pharmaceutical composition of the compound of formula (I), or a pharmaceutically acceptable salt thereof, which exhibits one or more, e.g. 1, 2 or 3, of the following desirable characteristics;

a dissolution profile which is suitable for the administration of the therapeutic agent,—a compression profile with a wide hardness window which still provides acceptable friability, hardness, disintegration time and dissolution;

sufficient stability to achieve a reasonable shelf life;

a relatively high drug loading, if desired, may easily be achieved.

The formulations of the present invention are also achievable via a robust manufacturing process; which gives good flowability, compactability, and which minimizes sticking problems and capping of tabletting mixtures on the rotary press. The process and the formulations are amenable to scale-up, with a reproducible performance.

The invention claimed is:

1. A pharmaceutical composition in the form of a tablet comprising
   a) a therapeutically effective amount of the sodium salt of the compound trans-(4-{4-[5-(6-trifluoromethyl-pyridin-3-ylamino)-pyridin-2-yl]-phenyl}-cyclohexyl)-acetic acid of formula (I);

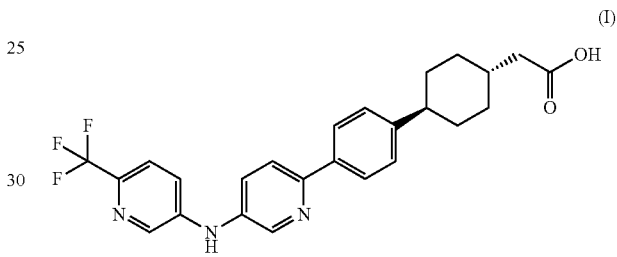

(I)

b) 2% of sodium lauryl sulfate by weight of the tablet prior to any optional film coating;
   c) 10% of hydroxypropyl cellulose by weight of the tablet prior to any optional film coating;
   d) 15 to 26% of microcrystalline cellulose by weight of the tablet prior to any optional film coating;
   e) 0.5% of colloidal silica by weight of the tablet prior to any optional film coating;
   f) 3% of sodium stearyl fumarate by weight of the tablet prior to any optional film coating;
   g) 20 to 85% of anhydrous lactose by weight of the tablet prior to any optional film coating;
   h) 2% of sodium starch glycolate by weight of the tablet prior to any optional film coating; and
   i) an optional film coating.

2. The pharmaceutical composition according to claim 1, further comprising 0.1 to 10% of magnesium stearate by weight of the tablet prior to any optional film coating.

3. The pharmaceutical composition according to claim 1, further comprising a surfactant selected from stearic acid, palmitic acid, myristic acid, poloxamers, polyethylene glycols, the Tween series of surfactants, the Brij series of surfactants, Triton X-100, and combinations thereof.

4. The pharmaceutical composition according to claim 1, further comprising a binder selected from polyethylene glycols, pregelatinized starch, starch, chitosan, guar gum, methyl cellulose, calcium carboxymethylcellulose, sodium carboxymethylcellulose, alginic acid, alginic acid sodium salt, hydroxypropylmethyl cellulose, hydroxypropyl cellulose and combinations thereof.

5. The pharmaceutical composition according to claim 1, wherein the ratio of microcrystalline cellulose to anhydrous lactose is between 1:5 and 1:1.

6. The pharmaceutical composition according to claim 1, further comprising croscarmellose sodium or cross-linked polyvinyl pyrrolidone as a disintegrant.

7. The composition of claim 1, wherein the hydroxypropyl cellulose has a viscosity from 3 to 6 cps.

8. The composition of claim 1, wherein the hydroxypropyl cellulose is low substituted hydroxypropyl cellulose (L-HPC LH-21).

9. The composition of claim 1, further comprising 0.05 to 5% of one or more glidants selected from magnesium trisilicate, powdered cellulose, starch, talc and combinations thereof by weight of the tablet prior to any optional film coating.

10. The composition of claim 1, wherein the film coating is comprised of hydroxypropyl methyl cellulose, polyethylene glycol and talc.

11. The composition of claim 10, wherein the film coating further comprises iron oxide.

12. The composition of claim 10, wherein the film coating further comprises titanium dioxide.

13. A process for preparing a pharmaceutical composition according to claim 1 comprising the steps of:
   (a) mixing the compound of the formula (I), or a pharmaceutically acceptable salt thereof, with at least one pharmaceutically acceptable excipient to form a blend;
   (b) roller compacting, then milling said blend;
   (c) lubricating the resulting mixture, and
   (d) compressing the resulting mixture into a solid oral dosage form.

* * * * *